United States Patent [19]

Bailey, Jr.

[11] Patent Number: 4,634,423

[45] Date of Patent: Jan. 6, 1987

[54] OPHTHALMOLOGICAL METHOD AND INSTRUMENT FOR IMPLANTATION OF POSTERIOR CHAMBER INTRAOCULAR LENS

[76] Inventor: Paul F. Bailey, Jr., 1955 NW. Northrup St., Portland, Oreg. 97209

[21] Appl. No.: 605,430

[22] Filed: Apr. 30, 1984

[51] Int. Cl.$^4$ .................................................. A61M 31/00
[52] U.S. Cl. .................................................. 604/51; 623/6
[58] Field of Search ......................... 604/15–18, 604/51, 27; 3/13; 128/303 R

[56] References Cited

U.S. PATENT DOCUMENTS

| 3,490,455 | 1/1970 | Illig | 128/303 R |
|---|---|---|---|
| 3,589,363 | 6/1971 | Banko | 604/27 |
| 4,122,556 | 10/1978 | Poler | 128/303 R |
| 4,136,406 | 1/1979 | Norris | 623/6 |
| 4,214,585 | 7/1980 | Bailey, Jr. | 128/303 R |
| 4,251,887 | 2/1981 | Anis | 128/303 R |
| 4,326,306 | 4/1982 | Poler | 623/6 |

FOREIGN PATENT DOCUMENTS 990912 9/1951 France ........................ 604/15

*Primary Examiner*—Dalton L. Truluck
*Assistant Examiner*—Mario Costantino
*Attorney, Agent, or Firm*—Kolisch, Hartwell & Dickinson

[57] ABSTRACT

An ophthalmological instrument for facilitating controlled insertion of an intraocular lens having resilient, open-loops into the posterior chamber of an eye includes a holder dimensioned for being held by a surgeon from which extends a loop-receiving member configured for receiving and deforming a first one of the loops from its normally nonstressed arcuate shape into a substantially straight and stressed condition. A displacement device associated with the loop-receiving member is selectively operable by the surgeon for displacing the first loop away from the loop-receiving member so that the stored energy in the loop imparts rotation to the lens as it is inserted into the posterior chamber of the eye.

5 Claims, 12 Drawing Figures

OPHTHALMOLOGICAL METHOD AND INSTRUMENT FOR IMPLANTATION OF POSTERIOR CHAMBER INTRAOCULAR LENS

BACKGROUND AND SUMMARY OF THE INVENTION

The present invention relates to ophthalmology, and more particularly to a novel method and instrument for facilitating controlled and precise implantation of an intraocular lens into the posterior chamber of an eye.

Over the last several years, it has become increasingly evident that implantation of posterior chamber intraocular lenses provides many advantages over implantation of anterior chamber lenses in patients who have had a cataractous lens removed by extracapsular extraction methods. While there are many different forms and models of posterior chamber lenses, most generally embody a lens having a plano-convex form which includes a pair of circular open-loops. Each loop extends from an attachment point on the periphery of the lens and has a free end. Generally, posterior chamber lenses include a pair of these loops, called "C" loops, "J" loops, etc., depending on their form. Suffice it to say that posterior chamber lenses have circular open-loops laterally-opposed which extend from the lens body for stabilizing and orienting the lens in the posterior chamber, or when the lens is in the "bag" (the membrane which remains after the cataractous lens has been removed).

While posterior chamber lenses provide certain advantages once they are implanted, it should be recognized that the actual implantation procedure is very difficult because of the minuteness of the eye. The basic problem resides in that the circular open-loops are dimensioned so that the greatest distance between them is significantly larger than the pupil opening—even when the pupil is dilated during surgery—thereby making it very difficult to insert the lens. Generally, a surgeon will grip either the lens or a first one of the loops (the superior loop) with a forceps and insert the other loop downwardly through the corneolimbus and the pupil opening. However, because the pupil opening is small, relative to the distance between the loops, the surgeon must then use some other type of tool to compress the superior loop toward the lens body in order that it may be slipped under the iris for affecting positioning of the lens into the posterior chamber. That step is very tricky, and requires great skill, inasmuch as the surgeon must regrasp the lens and use some type of force to compress the loop.

Various proposals have been made for facilitating this step, several of which include providing various configurations such as eyelets or notches on the superior loop which is second to enter the posterior chamber. The notches and eyelets are configured for engaging a specialized tool so that the loop can be pushed or compressed toward the lens. In addition, various types of lenses are provided with holes, adjacent the periphery of the lens body, so that they may be gripped or stabilized by other types of tools: the whole purpose is to provide lens constructions and loops with the capability of being held and repositioned during maneuvering of the lens into the posterior chamber. However, it should be evident that no matter how the lens loop is configured or whether or not the lens body includes holes, the surgeon must go through the following steps: (1) the surgeon must grip the lens and insert one loop into the posterior chamber; (2) the lens must be regripped and the superior loop compressed while the surgeon rotates the lens inwardly.

While a skillful surgeon may accomplish the above steps, a very considerable problem is presented when the loop is compressed as described above. During the compression step, which is necessary in order for the superior loop to be pressed down behind the iris, the other loop inadvertently may be pushed too hard against the "bag," thereby breaking same which completely destroys the bag's ability to provide support for the lens. The problem is critical, and is compounded by the fact that as the surgeon rotates the lens into position, the pressure exerted against the lens continuously presents the risk of breaking the bag.

Accordingly, it is a general object of the present invention to provide an ophthalmological method for facilitating controlled and precise insertion during implantation of an intraocular lens into the posterior chamber of an eye. The present invention contemplates that the posterior chamber lens will include a pair of circular open-loops, and utilizes the concept of elastically deforming a first one of the loops from its normally nonstressed arcuate shape until it is substantially straight, whereby it is biased into a stressed condition. This is accomplished by providing a novel instrument which includes a tubular member or needle which receives the loop and straightens it into the aforementioned stressed condition. Then, continuing on with the method of the present invention, the other loop is at least partially inserted into the posterior chamber and the straightened or captured loop is pushed outwardly through the tubular member whereby it is rotatably displaced into the posterior chamber. The rotatable displacement is accomplished by, in effect, releasing the loop from its stressed condition.

The above method is very simple, can be practiced very readily and ensures controlled and precise positioning or insertion of the intraocular lens into the posterior chamber. No regripping, or regrasping or compression of a loop is required, and the intraocular lens is automatically rotated into precise position.

Another object of the present invention is to provide an instrument, as described above, which is relatively simple in construction and which will permit ease of handling by a surgeon and enable the controlled insertion. To this end, the present invention contemplates that the instrument includes a holder for gripping by the surgeon. The tubular member extends from the holder and is dimensioned with a length and internal diameter suitable for receiving the loop and deforming it elastically into a substantially straight configuration.

It is another object of the present invention to provide an instrument, as described above, in which there is a displacement means, preferably in the form of a plunger element, which is coaxially mounted and movable within the tubular member selectively operable for displacing the loop away or outwardly from the tubular member so that the stored energy in the loop which causes the loop to reassume its arcuate shape will cause the lens to rotate as it is being implanted into the posterior chamber.

Still another object of the present invention is to provide an instrument, as described above, in which the tubular member is defined by an assembly which includes a first outer cannula within which is coaxially mounted a second inner cannula to define an intermediate and elongate annular chamber for transferring irrigation fluid into the eye. The advantage of that construction is that the integrity of the anterior chamber can be maintained, by the irrigation fluid, during the implantation procedure.

These and additional objects and advantages of the method and instrument of the present invention will be more readily understood after a consideration of the drawings and the following detailed description of the preferred embodiment.

DETAILED DESCRIPTION OF THE PREFERRED EMBODIMENT

As mentioned at the outset, it is a general object of the present invention to provide an ophthalmological method and instrument for facilitating surgical implantation of an intraocular lens ("IOL") into the posterior chamber of an eye by elastically deforming a first one of the resilient, open-loops of the IOL from its normally nonstressed arcuate shape to a substantially straight orientation. With the loop so held, it is biased into a stressed condition and the IOL may be oriented by a surgeon into a position whereby the other loop is at least partially inserted into the posterior chamber, thereafter, the first loop is released from its stressed condition and as it returns to its arcuate shape, it rotatably displaces the lens into the posterior chamber.

Figure 1:
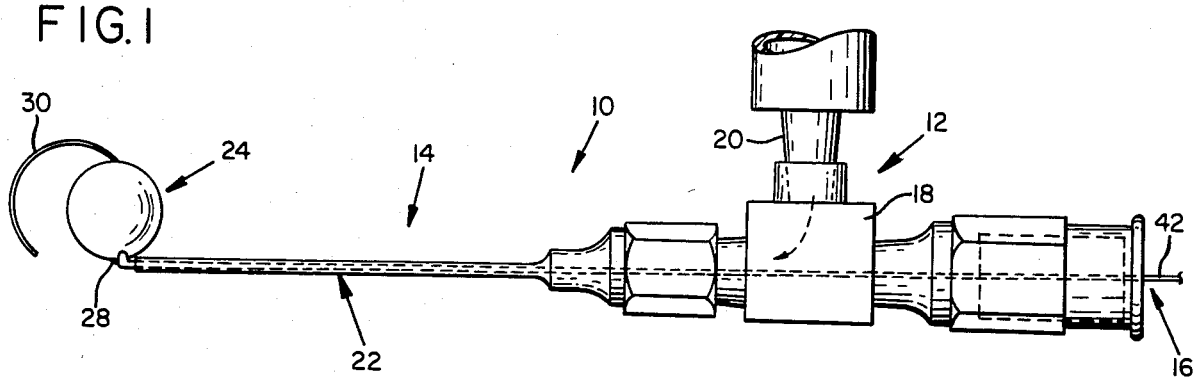
FIG. 1 is a side elevational view, greatly enlarged, of an instrument according to the present invention showing how it is used to capture one of the loops of a posterior chamber intraocular lens.

The specific instrument for practicing the method outlined above is generally indicated at 10 in FIG. 1, and includes a holder generally indicated at 12 which is dimensioned for being held or grip by the surgeon. A loop-receiving means 14 is connected to the holder and is configured for receiving and deforming one of the loops of an IOL in a manner which will be described shortly hereafter. A displacement means, generally indicated at 16, is associated with loop-receiving means 14 and is selectively operable for displacing one of the loops as will become evident. It will be noted that holder 12 includes a central or hub section 18 and interconnected at right angles thereto is a fitting 20. The purpose of fitting 20, which is only partially shown, is to admit irrigation fluid into the hub, and eventually downwardly through the loop-receiving means for injection into the eye's anterior chamber.

With respect to further details of instrument 10, attention will now be directed to the specific construction of loop-receiving means 14 which may be thought of as a "needle assembly" defined by an elongate tubular member 22 which extends from the holder and is dimensioned so that its length and internal diameter are suitable for receiving one of the loops of an IOL. Specifically, as shown in FIG. 2A, an IOL, generally indicated at 24, suitable for positioning in the posterior chamber, includes a plano-convex lens body 26 and a pair of laterally-opposed and circular open-loops, a first one of which is indicated at 28 and the other indicated at 30.

While the arcuate form of the loops varies between different manufacturers' models, it is generally the case that posterior chamber IOLs have open-loops of some type of circular configuration. In any event, it is the purpose of the present invention to initially stress one of the loops, such as first loop 28, from its normally nonstressed arcuate shape into a substantially straight and stressed condition, and tubular member 22 is provided to achieve that end. Specifically, as shown in FIG. 2, tubular member 22 is defined by a tubular assembly which includes a first outer cannula 32 within which is coaxially mounted a second inner cannula 34.

It is seen that inner cannula 34 is dimensioned with an overall outer diameter less than that of the inner diameter of outer cannula 32, thereby to define an intermediate and elongate annular chamber 36 which enables transferring of irrigation fluid into the eye. Inner cannula 34 is fixed relative to outer cannula 32 and may be provided with a retainer mean such as a notch or recess 38 for receiving and holding a portion of lens body 26. It also includes an iris retraction means 40 which functions in a manner to be described at a later point. As shown in FIG. 2, IOL 24 is held so that first loop 28 is inserted into bore 34a of inner cannula 34 so that the loop has been elastically deformed from its normally nonstressed arcuate shape (shown in FIG. 2A) until it is substantially straight and biased into a stressed condition. A portion of lens body 26 is inserted into recess 38, which enables the lens body to be controlled by the surgeon. As shown in FIGS. 1 and 2, a forward portion of inner cannula 34, such as ends 35, 35a, may be curved, offset or angled from the longitudinal axis of tubular member 22 in order to grip lens body 26 by overlapping upper and lower segments thereof.

Figure 2:
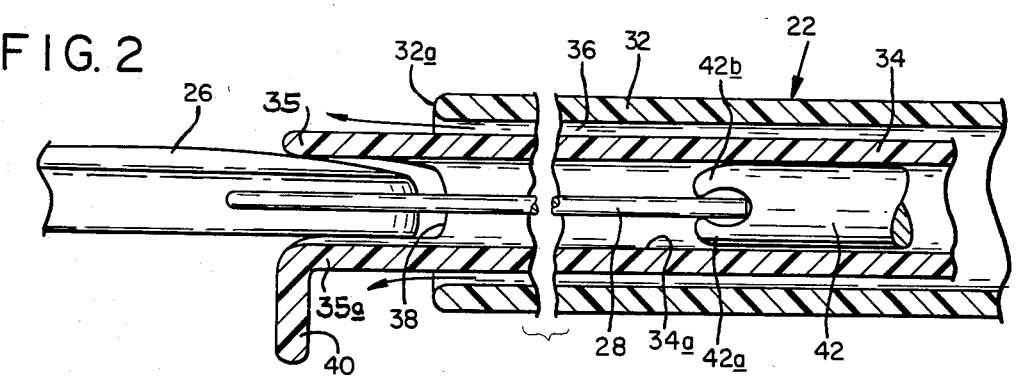
FIG. 2 is a further enlarged view, taken in longitudinal and fragmentary cross section of an end of the instrument, showing insertion of the loop.
Figure 2A:
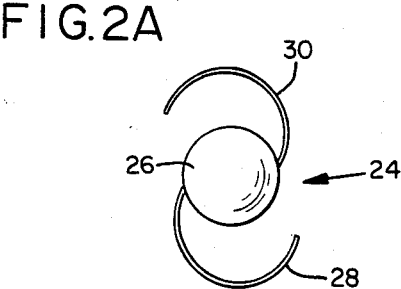
FIG. 2A is an enlarged view of a posterior chamber intraocular lens.

It will be noted from viewing FIG. 2 that first loop 28 abuts against displacement means 16, which takes the form of a plunger element 42 slidably disposed within tubular member 22, in inner cannula 34, and is selectively operable for engaging the first loop and shifting it coaxially until it emerges completely from the free end of inner cannula 34. Plunger element 42 is shown in one form in FIG. 2 whereby it includes resilient clamping fingers or portions 42a, 42b which, when they exit from the free end of inner cannula 34, splay outwardly for releasing first loop 28. However, the end of plunger element 42, which engages first loop 28, may be merely an abutting surface, because it is only necessary to provide some type of shiftable plunger element which will engage the inserted free end of first loop 28 so that the loop can be shifted outwardly from its capture within loop-receiving means 14. As shown in FIG. 1, plunger element 42 extends outwardly from the right hand side of holder 12 so that it may be gripped by a surgeon. Of course, the exterior end of plunger element 42 may be configured in different shapes for ease of gripping, and FIG. 1 does not include those shapes because such are largely dependent on surgeon preference.

Use of the Ophthalmological Instrument

Figure 8:
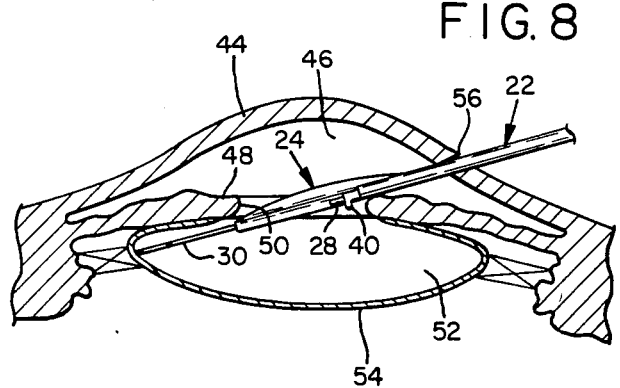
FIG. 8 is a cross-sectional view taken along lines 8—8 of FIG. 7 and illustrates partial insertion of the intraocular lens into the posterior chamber.

A description will proceed now on the use of instrument 10 for facilitating controlled and precise manipulation of an IOL during implantation into the posterior chamber of an eye. This description will refer to FIGS. 3-11 which illustrate, in continuous sequence, how an IOL is implanted using the present method and instrument. Initially turning to FIG. 8, the anatomy of a human eye, as viewed in cross section, will be discussed. The cornea is indicated at 44, the anterior chamber at 46, the iris at 48, pupil opening at 50, and the posterior chamber at 52. The membrane, after the cataractous lens has been removed by a suitable extracapsular extraction method, is indicated at 54. That membrane defines what is referred to as the "bag."

Figure 3:
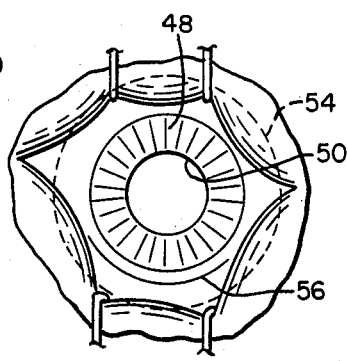
FIGS. 3-7 illustrate, in sequential order, the steps involving implantation of an intraocular lens into the posterior chamber.
Figure 4:
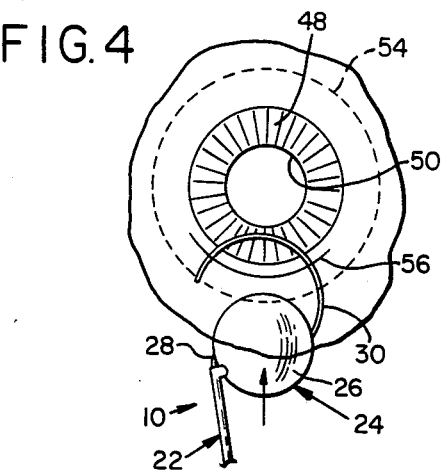

With reference to FIG. 3, which is a view of the eye taken from above, it can be seen that the upper and lower lids have been suitably pulled back by appropriate clamps. Previously, the cataractous lens has been removed, as by phacoemulsification or other method, thereby leaving membrane 54 which defines the "bag." It is an object now to implant an IOL, such as IOL 24, into the "bag" without tearing or damaging same, and this is where instrument 10 comes into play. The surgeon uses the instrument by first inserting the end of first loop 28 into tubular member 22, and specifically into inner cannula 34. Because the inner cannula is cylindrical, i.e., it is dimensioned with a straight longitudinal axis, first loop 28 is bent, or elastically deformed, from its normally nonstressed arcuate or circular shape until it is substantially straight, thereby being biased into a stressed condition whereby it is under tension. The IOL is positioned within recess 38, and the surgeon manipulates the instrument so that the other loop, such as indicated at 30, is directed through corneolimbus 56. This initial step is shown in FIG. 4, and it can be seen that loop 30 has been partially pushed through the opening defined by corneolimbus 56. The surgeon now proceeds to advance IOL 24 toward pupil opening 50. At this time, plunger element 42 has not been actuated, and first loop 28 is engaged as shown in Fig. 2, or if flexible gripping members 42a, 42b are not provided, then an end of plunger element 42 abuts against the end of first loop 28.

Figure 5:
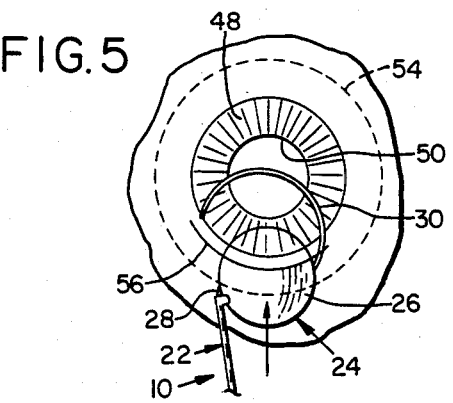
Figure 6:
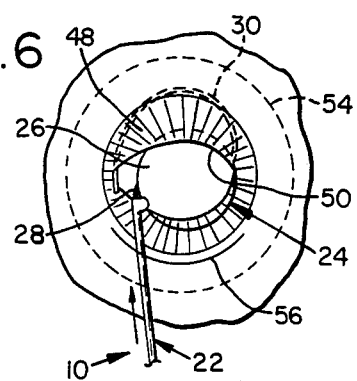
Figure 7:
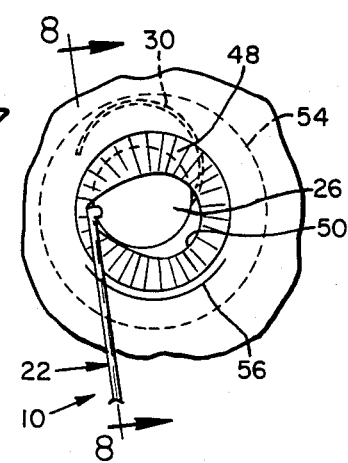

As shown in FIG. 5, the surgeon has fed IOL 24 further through corneolimbus 56 by exerting, primarily, a rectilinear force on instrument 10. As shown in FIG. 6, loop 30 has been pushed through pupil opening 50 and the end of tubular member 22 is positioned adjacent the pupil opening. Next, as shown in FIG. 7 (also view the cross-sectional view of FIG. 8), the IOL has been further pushed into the pupil opening and loop 30 is disposed within posterior chamber 52. At this juncture, the surgeon manipulates plunger element 42 so as to exert a force against first loop 28 to thereby shift the loop coaxially along inner cannula 34.

Figure 9:
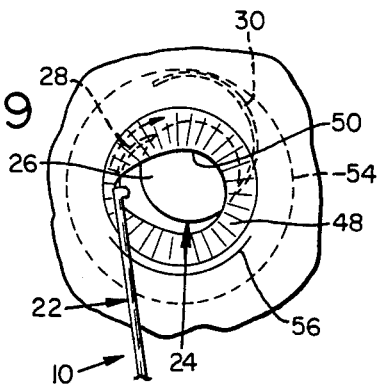
FIGS. 9-11 illustrate, in sequential order, final insertion of the intraocular lens into the posterior chamber using the instrument and method of the present invention.
Figure 10:
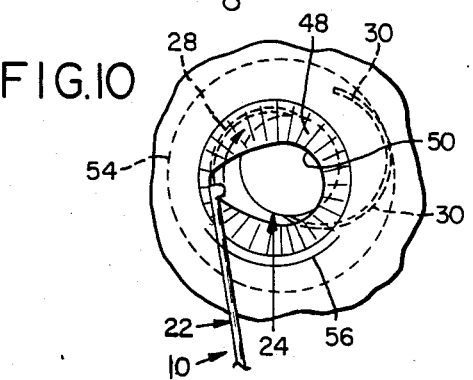

As first loop 28 is shifted along inner cannula 34, lens body 26 will be released from recess 38 and will begin to rotate. The stored energy within the loop causes the loop to reassume its prior arcuate shape, as it emerges from inner cannula 34, and the IOL begins to rotate as shown in FIG. 9. As shown in FIG. 10, plunger element 42 has been further extended, toward the end of inner cannula 34, and the lens rotates further, with loop 30 sliding, due to its arcuate form, along the surface of the "bag."

Figure 11:
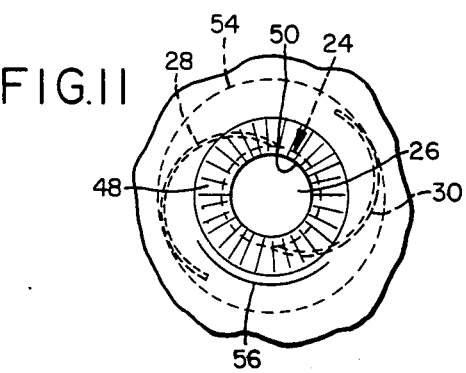

FIG. 11 shows IOL 24 fully inserted into the posterior chamber, and it should be appreciated that first loop 28 and loop 30 are in a relatively nonstressed state, inasmuch as there are no significant compressive forces being exerted thereon.

What has been described is a very simple method which may be used by a surgeon for implanting an IOL in which insertion into the posterior chamber is accomplished without having to grab, release, and regrab the lens using a variety of different tools in order to ensure implantation into the posterior chamber. Rather, as should be appreciated from the above, the surgeon only needs to actuate plunger element 42 to affect a precise, and very controlled implantation of an IOL.

Moreover, it will be observed that suitable irrigation fluid may be transferred through annular chamber 36 via fitting 20 from a source (not shown) to maintain the integrity of anterior chamber 46. In addition, the iris retraction means, which is representing by depending element 40, may be advantageously employed to pull back the iris, as the need may dictate, in order to enlarge the pupil opening during implantation. This step may occur when it is desired to provide a further means for ensuring precise insertion of the IOL, without pushing or otherwise applying dangerous forces to the lens body or the loops which could cause breakage or tearing of the "bag."

While the present invention has been shown and described with reference to the aforegoing preferred embodiment, it will be appreciated by those skilled in the art that other changes in form and detail may be made therein without departing from the spirit and scope of the invention as defined in the appended claims.

It is claimed and desired to secure by Letters Patent:

1. An ophthalmological method for facilitating controlled insertion of an intraocular lens having resilient, openloops into the posterior chamber of an eye comprising:

elastically deforming a first one of the loops from its normally nonstressed arcuate shape until it is substantially straight and biased thereby into a stressed condition;

orienting the lens into a position whereby the other loop is at least partially inserted into the posterior chamber; and rotatably displacing the lens into the posterior chamber by releasing the first loop from its stressed condition.

2. The method of claim 1 wherein the elastically deforming step is defined by inserting the first loop, free end first, into an elongate, tubular member.

3. The method of claim 2 wherein the rotatably displacing step is defined by directing a force against the first loop so that as it emerges from the tubular member, the lens is rotated into position by the stored energy of the first loop as it returns to its normally nonstressed arcuate shape.

4. The method of claim 3 wherein the displacing step is further defined by directing the force against the end of the first loop inserted in the tubular member.

5. The method of claim 4 wherein the rotatably displacing step is defined by rotation generally in the range of 90°-360° about an axis extending concentrically through the lens.

* * * * *